(12) United States Patent
Sauer et al.

(10) Patent No.: US 6,337,300 B1
(45) Date of Patent: *Jan. 8, 2002

(54) SHAPED METAL FIXED-BED CATALYST, A PROCESS FOR ITS PREPARATION AND ITS USE

(75) Inventors: Jörg Sauer, Rodenbach; Thomas Haas, Frankfurt; Bruno Keller, Wackernheim; Andreas Freund, Kleinostheim; Werner Burkhardt, Brachttal; Dietrich Michelchen, Erlensee; Monika Berweiler, Maintal, all of (DE)

(73) Assignee: Degussa AG, Hanau (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/081,568

(22) Filed: May 19, 1998

(30) Foreign Application Priority Data

May 26, 1997 (DE) .......................................... 197 21 897

(51) Int. Cl.[7] .............................. B01J 25/00; B01J 25/02
(52) U.S. Cl. ...................... 502/301; 502/300; 502/325; 502/337; 502/338
(58) Field of Search ................................ 502/300, 301, 502/325, 337, 338

(56) References Cited

U.S. PATENT DOCUMENTS

| 3,997,478 A | * | 12/1976 | Petro .......................... 502/301 |
| 4,153,578 A | | 5/1979 | De Thomas et al. |
| 4,826,799 A | | 5/1989 | Cheng et al. ................. 502/301 |
| 5,536,694 A | * | 7/1996 | Schuetz et al. ............. 502/301 |
| 5,733,838 A | * | 3/1998 | Vicari et al. ................. 502/335 |

FOREIGN PATENT DOCUMENTS

| DE | 2101856 | | 11/1974 |
| DE | 2100373 | | 4/1978 |
| DE | 2053799 | | 10/1981 |
| DE | 4007345 | A1 | 9/1991 |
| DE | 0648534 | A1 | 9/1994 |
| DE | 4446907 | A1 | 7/1996 |
| EP | 0648534 | A1 | 4/1995 |
| EP | 0771784 | A1 | 5/1997 |
| EP | 0842699 | A2 | 5/1998 |

OTHER PUBLICATIONS

Curry–Hyde et al., "Improvements to Raney Copper Methanol Synthesis Catalysts through Zinc Impregnation. Pore Structure and the Influence on Activity", XP002065792, Applicant Catalysis, Bd. 95, 1993, pp. 65–74.

* cited by examiner

Primary Examiner—Elizabeth D. Wood
(74) Attorney, Agent, or Firm—Smith, Gambrell & Russell LLP

(57) ABSTRACT

A shaped metal fixed-bed catalyst is disclosed which contains at least one catalyst alloy formed of a catalyst metal and an extractable alloying component. The catalyst is activated in an outer layer with a thickness of 0.1 to 2.0 mm starting from the surface by complete or partial extraction of the extractable alloying component. The catalyst may also contain promoters. The catalyst is distinguished from known catalyst in that it is formed exclusively of the catalyst alloy and has a total pore volume of 0.1 to 0.6 ml/g. The catalyst is used for hydrogenation, dehydrogenation and hydrogenolysis reactions.

29 Claims, No Drawings

SHAPED METAL FIXED-BED CATALYST, A PROCESS FOR ITS PREPARATION AND ITS USE

INTRODUCTION AND BACKGROUND

The present invention relates to a shaped, Raney metal fixed-bed catalyst which contains at least one catalyst alloy made of a catalyst metal and an extractable alloying component, wherein the catalyst is activated in a surface layer with a thickness of 0.1 to 2.0 mm starting from the surface of the shaped catalyst by complete or partial extraction of the extractable alloying component and which optionally contains promoters.

In a further aspect, the present invention also relates to a process for preparing the catalyst by mixing a powder of the catalyst alloy and a high molecular weight polymer, shaping the mixture to form shaped articles and removing the polymer by thermal treatment and calcining the shaped articles at temperatures of less than 850° C. Still further, the present invention also relates to use of the aforementioned catalyst for hydrogenation, dehydrogenation and hydrogenolysis reactions.

Activated metal catalysts are known in the field of chemical engineering as Raney catalysts. They are used, generally in powdered form, for a large number of hydrogenation reactions of organic compounds.

These powdered catalysts are prepared from an alloy of a catalytically active metal, which in the following description is also called a catalyst metal and a further alloying component which is soluble in alkalis. Nickel, cobalt, copper or iron are mainly used as catalyst metals. Aluminum is largely used as the alloying component which is soluble in alkalis, but other components may also be used, in particular zinc and silicon are also suitable.

This so-called Raney alloy is first finely milled in accordance with Raney's method. Then the aluminum is removed entirely or partly by extracting with alkalis such as, for example, caustic soda solution.

This process activates the alloy powder. Due to extraction of the aluminum, the alloy powder has a high specific surface area, between 20 and 100 m$^2$/g (BET), and is rich in adsorbed hydrogen. The activated catalyst powder is pyrophoric and is stored under water or organic solvents or embedded in high boiling organic compounds.

Powdered catalysts have the disadvantage that they can only be used in batch processes and have to be isolated after the catalytic reaction by filtering the reaction medium, a costly process. Therefore a number of processes for preparing shaped articles which lead to activated metal fixed-bed catalysts after extraction of the aluminum have been disclosed.

U.S. Pat. No. 4,826,799 describes the preparation of activated Raney metal fixed-bed catalysts by mixing a powder of the alloy of catalyst metal and aluminum with an organic polymer and optionally a shaping aid, shaping this mixture by extrusion or compression to give the desired shaped articles and calcining the shaped articles in air at temperatures above 850° C. This leads to a pore structure in the shaped article, due to combustion of the added organic material, and to the formation of α-aluminum oxide which acts as a ceramic binder between the alloy particles and provides the shaped articles with the desired mechanical stability. Then the shaped articles are activated by extracting the remaining aluminum which has not been oxidized during calcination.

A critical feature of this process is the formation of α-aluminum oxide between the alloy particles as a ceramic binder. α-aluminum oxide, in contrast to γ-aluminum oxide and aluminum, is not soluble in alkalis and is therefore not dissolved out during activation of the shaped article with caustic soda solution.

Catalysts prepared in accordance with U.S. Pat. No. 4,826,799 have serious disadvantages. In order to form α-aluminum oxide, the shaped articles must be calcined at a temperature above 850° C. In fact, below 850° C. no α-aluminum oxide but only γ-aluminum oxide, which is soluble in alkalis, is formed. The α-aluminum oxide used as binder is catalytically inactive and thus reduces the catalyst activity. During calcination a well-sealed or less well-sealed sealed layer of this inactive material which is insoluble in alkalis is formed on the surface of the alloy particles. Thus activation of the alloy is made very difficult. In the final catalyst, this layer represents a diffusion barrier for reactant molecules, which results in a further loss in activity.

In addition, it is expected of modern catalyst systems that they should be easy to reclaim for re-use, in order to protect the environment. Processing of ceramically bonded metal fixed-bed catalysts however is difficult due to the insoluble ceramic binder.

EP 0 648 534 A1 describes the preparation of an activated metal fixed-bed catalyst which is produced without α-aluminum oxide as a binder. The catalyst is obtained by shaping a powder of at least one catalyst alloy with a powder of the pure catalyst metal, with the addition of shaping aids and pore producers, and then calcining at temperatures of less than 850° C. During calcination the shaping aids and pore producers are burned away. The alloy powder and metal powder sinter together to provide mechanically stable and porous shaped articles. These shaped articles thus consist of particles of the catalyst alloy which are bonded by a powder of the pure catalyst metal. They do not contain any catalytically inactive ceramic binder. The shaped articles are activated in a surface layer by extracting the aluminum contained in the catalyst alloys with caustic soda solution.

Although the pure catalyst metal used as binder in this catalyst also makes a certain contribution to the catalytic activity of the catalyst, its contribution is negligible due to the low specific surface area of this material. Thus the catalytic activity of the catalyst, with respect to the total weight of catalyst, is lower than it would be if the catalyst metal were not used as a binder.

EP 0 648 534 A1 recommends using, as binder, a powder of the pure catalyst metal with a particle size which is less than the particle size of the alloy powder in order to increase the strength of the catalyst-shaped articles. This leads to relatively dense catalysts with small pore volumes. EP 0 648 534 A1 does not mention the bulk densities of the catalysts. Fixed-bed catalysts prepared by this procedure, however, have very high bulk densities of about 2 kg/l.

Thermoplastic materials for preparing metallic shaped articles are disclosed in DE 40 07 345 A1. The materials contain A) a sinterable powdered metal or a powdered metal alloy, B) a mixture of B1) a polyoxymethylene homopolymer or copolymer and B2) a polymer, homogeneously dissolved in B1) or dispersed in B1) with an average particle size of less than 1 μm, as binder and a dispersing aid. These materials may be shaped to give shaped articles. In order to remove the binder, the freshly prepared shaped articles obtained after shaping are treated under a gaseous acid-containing atmosphere. Treatment is performed until at least 80% of the polyoxymethylene fraction has been removed.

Then the product obtained in this way is heated to 250 to 500° C. in order to completely remove the remainder of the binder which is still present. The binder-free product can be converted into a metallic shaped article by sintering, the final product being free of cracks and pores even when the walls are thick.

An object of the present invention therefore is to provide a shaped, metal fixed-bed catalyst which has a substantially lower bulk density than comparable catalysts known from the prior art for the same or better hydrogenation activity.

SUMMARY OF THE INVENTION

The above and other objects of the present invention are achieved by a shaped metal fixed-bed catalyst which contains at least one catalyst alloy consisting of a catalyst metal and an extractable alloying component and optionally promoters. The catalyst is characterized in that it consists exclusively of the catalyst alloy(s), has a total pore volume of 0.1 to 0.6 ml/g and is activated in a surface layer with a thickness of 0.1 to 2.0 mm starting from the surface by complete or partial extraction of the extractable alloying component.

Thus the catalyst of the invention does not contain, in comparison to catalysts according to EP 0 648 534 A1, any less-active pure catalyst metal as a binder. In addition it has a higher pore volume than the known catalyst when using the same alloy powder, which means that a thicker activated outer layer is produced when using the same activation conditions. These differences result in a higher specific activity of the catalyst according to the invention both with respect to its weight and also to its bulk density.

Nickel, cobalt, copper or iron are preferably used as catalyst metals and aluminum, zinc or silicon are used as extractable alloying components. The ratio by weight of catalyst metal to extractable alloying component in the catalyst alloy is, as is conventional with Raney alloys, in the range from 30:70 to 70:30.

DETAILED DESCRIPTION OF INVENTION

The present invention will now be described in greater detail. Catalysts according to the invention may be doped with other metals in order to modify their catalytic activity. The purpose of this type of doping is, for example, to improve the selectivity in a specific reaction. The doping metals are frequently called promoters. The doping and promoting of Raney catalysts are described, for example, in U.S. Pat. No. 4,153,578, in DE-AS 21 01 856, in DE-OS 21 00 373 and in DE-AS 20 53 799 which are all relied on an incorporated herein by reference. Suitable promoters are chromium, iron, cobalt, tantalum, titanium and/or molybdenum and also metals from the platinum group. They are expediently added as alloying constituents in the catalyst alloy. They are typically present in the catalyst alloy in amounts of up to 15 wt. %. When doping with molybdenum, it is expedient to perform the doping procedure only after activating the catalyst. For this purpose, the final catalyst is introduced into a molybdate solution at elevated temperature, e.g. at 80° C. Depending on the duration of the treatment, a specific amount of molybdenum compound is adsorbed by the catalyst.

An activated fixed-bed catalyst is prepared in accordance with the invention by mixing an alloy powder consisting of a catalytically active catalyst metal, optionally promoters and an extractable alloying component with a high molecular weight polymer, shaping the mixture to give freshly prepared shaped articles and removing the polymer by thermal treatment and calcining the freshly prepared shaped articles at temperatures of less than 850° C. and activating the shaped articles obtained by extracting the extractable alloying component using caustic soda solution. A polyoxymethylene homopolymer or copolymer moulding compound is suitable for use as the high molecular weight polymer, this being decomposed by thermal treatment at temperatures between 100 and 300° C. In the following the expression polyoxymethylene (POM) is used instead of polyoxymethylene homopolymer or polyoxymethylene copolymer moulding compounds and is intended to be an all inclusive term. Polyoxymethylene and methods for its preparation are known to a person skilled in the art and are described in the literature.

The polyoxymethylene acts as a binder for the freshly prepared shaped articles and as a pore producer. It is mixed directly with the catalyst alloy. It has been shown that when using polyoxymethylene with a melt volume index MVI (according to DIN ISO 1133, measured at 190° C. with a load of 2.16 kg) between 1 and 50, preferably in the range from 5 to 13, in particular in the range from 6 to 9, further additives are generally not required during the mixing. The MVI flow index represents adequate characterization of polyoxymethylene for the purposes of the present invention.

Use of POM with an MVI of less than one has been proven to be non-beneficial due to the reduced viscosity of the molten material during the mixing procedure with the catalyst alloy. The use of POM with an MVI of greater than 50 leads to failure due to the poor binder properties in the mixture.

The catalyst alloy and polymer are kneaded in the form of powders at 180 to 250° C. to give a shapeable material. The primary particle size distribution of the alloy powder used is substantially unchanged during this procedure. Therefore no milling takes place. The objective of this preliminary treatment is to prepare the mixture for the subsequent shaping procedure. Extrusion, tabletting and compacting may be used for example. The mixture is preferably extruded to give extrudates with diameters of about 1 to 8 mm which are broken into approximately 2 to 5 mm long pieces. In the case of extrusion, the alloy powder and polymer are fed separately to the extruder. Mixing of the two components takes place in the extruder.

The average particle size of the catalyst alloy used is preferably in the range from 30 to 120 $\mu$m. Particle diameters of less than 30 $\mu$m lead to shaped articles with too low a porosity for use as catalysts. If the particle diameters are greater than 120 $\mu$m, the porosity is too high and the strength of the shaped articles decreases. The polyoxymethylene is preferably added to the mixture in an amount of 5 to 100 wt. %, with respect to the amount of catalyst alloy.

The freshly prepared shaped articles obtained by the shaping procedure are subjected to thermal treatment in order to decompose the polyoxymethylene to substantially formaldehyde and to drive it out of the freshly prepared shaped article. Decomposition of polyoxymethylene starts at temperatures above about 100° C. In order to avoid cracking the freshly prepared shaped articles by too vigorous release of the gaseous decomposition products the shaped articles should be warmed up appropriately slowly. Rates of decomposition of about 6 to 10 grams of decomposition products per kilogram of polyoxymethylene used per minute have proven suitable. These rates of decomposition can be set by adjusting the temperature in an appropriate manner. If the temperature is maintained at a constant value, the rates of decomposition decrease with increasing decomposition. In order to accelerate complete decomposition, it is therefore recommended that the temperature be increased continuously during the decomposition procedure in order to maintain the rate of decomposition at a constant level during the entire decomposition process. The decomposition process then terminates, depending on the rate of decomposition selected, after 170 to 200 minutes. Experience has shown that the temperature of the freshly prepared shaped articles has to be raised from 100° C. to about 300° C.

The freshly prepared shaped articles may thus be initially heated relatively rapidly to about 100° C. Then the temperature is increased to 300° C. in a controlled manner which ensures slow decomposition of the polyoxymethylene. If the freshly prepared shaped article is heated too rapidly to 300° C. the polyoxymethylene decomposes too suddenly and the shaped article is destroyed. After completing the decomposition process, the temperature of the freshly prepared shaped articles is increased to the calcination temperature of preferably 800° C. over the course of about 100 to 140 minutes. The freshly prepared shaped articles are then calcined at this temperature for 60 to 180 minutes.

The best temperature gradient for decomposition of the polyoxymethylene may be determined by a person skilled in the art in a few preliminary tests. It has to be taken into account while performing these that the porosity of the final catalyst may also be affected to some degree by the temperature gradient. In fact, due to decomposition of the polyoxymethylene, the freshly prepared shaped article becomes somewhat distended. As described above, however, this procedure must not be allowed to lead to complete destruction of the freshly prepared shaped article. It may be used in a targeted manner, however, in order to adjust the porosity of the final catalyst shaped article.

Decomposition of the polyoxymethylene may be performed under air. In order to support the decomposition process, however, it may also be performed, as described in DE 40 07 345 A1, in an acid-containing atmosphere. Suitable acids for use during the treatment are inorganic or organic acids which are volatile at the temperatures used. Suitable acids are for example nitric acid, formic acid or acetic acid.

Calcination of the freshly prepared shaped articles may also be performed in air. Restricting the calcination temperature to values below 850° C. ensures that any aluminum oxide formed is present only in the form of γ-aluminum oxide which is dissolved out of the shaped articles during subsequent activation.

For activation, the shaped articles are treated, after cooling, in a 20 wt. % strength solution, preferably caustic soda solution, at a temperature of 80° C. for a period of 120 minutes. This dissolves out the extractable alloying component contained in the catalyst alloy, usually aluminum. The extraction process progresses from the surface of the shaped article inwards. Using the values cited for the concentration of caustic soda solution, its temperature and the period of treatment, activated outer layers with a thickness of about 0.8 mm are obtained when the pore volume for the shaped article is 0.3 ml/g. The thickness of the outer layer can be varied between certain limits by changing the parameters mentioned above. The extraction parameters mentioned are thus not fixed values but may be adjusted by a person skilled in the art in accordance with his requirements. After the extraction procedure the shaped articles are washed alkali-free with water and stored under water until they are used.

The process described enables the preparation of an activated metal fixed-bed catalyst which consists entirely of the catalyst alloy. Compared with the catalyst described in EP 0 648 534 A1, it therefore does not contain, surprisingly, any pure catalyst metal as a binder and thus has a higher volume-specific activity. It has also been shown that on the whole catalysts with lower bulk density than those in EP 0 648 534 A1 are produced using this process. This is particularly advantageous in the case of expensive catalyst metals such as cobalt.

The catalyst according to the invention can be used for hydrogenation, dehydrogenation and hydrogenolysis of organic and inorganic substrates. Using the catalyst according to the invention, for example, nitro compounds, imines, nitriles, CC double and CC triple bonds, aromatic and heteroaromatic rings, carbonyl compounds and epoxides, also CO and $CO_2$, can be hydrogenated using hydrogen under conditions which are conventional for these types of hydrogenation reactions. Furthermore, for example, alcohols can be dehydrogenated to give carboxylic acids and aminoalkanols can be dehydrogenated to give aminocarboxylic acids.

A particularly preferred use is directed towards a process for preparing isophorone diamine (IPDA) from isophorone nitrile, wherein, in a first stage, isophorone is converted into the corresponding iminonitrile using ammonia in the presence of an acid imination catalyst in a manner known per se and this is hydrogenated and amminated, in a second stage, in the presence of the catalyst according to the invention to give isophorone diamine. The first stage is performed in the presence or absence of a solvent, preferably in the presence of a lower alcohol, at 0 to 100° C., for example in accordance with DE patent application 196 27 265.3 in the presence of an organo-polysiloxane which contains sulphonate groups as an imination catalyst. In the second stage the reaction mixture from the imination stage is passed over the catalyst according to the invention, preferably using a trickle-bed procedure at a pressure of 3 to 10 Mpa, wherein the reaction temperature is either 80 to 150° C. or initially 10 to 90° C. and then more than 90 to 150° C. Further details relating to process management may be obtained from the publications DE 43 43 890 A1 and DE 43 43 891 which are relied on and incorporated herein by reference.

EXAMPLE 1

An activated cobalt catalyst was prepared using a cobalt/aluminum alloy with 50 wt. % of aluminum, with respect to the total weight of the alloy, using the process described. The average particle size of the cobalt was 60 μm.

A mixture consisting of 15 wt. % of a polyoxymethylene copolymer and 85 wt. % of the cobalt/aluminum alloy was prepared at room temperature and extruded at a temperature of 190° C. with a mass flow of 10 kg/h in a double shaft extruder (Werner and Pfleiderer; Extruder ZSK 30). The polyoxymethylene copolymer contained 2.7 wt. % of butanediol formal as a copolymer (Ultraform® N2320) and had an MVI (190° C., 2.16 kg) of 6.7 to 8.5.

To decompose the polyoxymethylene, the freshly prepared shaped articles were first heated up to 120° C. over the course of 10 minutes in a furnace. Decomposition was then performed with a continuous increase in temperature from 120 to 280° C. over the course of 90 minutes. After this time the decomposition had largely terminated. Then the temperature was increased to 800° C. over the course of 125 minutes. The freshly prepared shaped articles were calcined at this temperature for a further 140 minutes.

After cooling the shaped article, it was activated in caustic soda solution (20 wt. %) at a temperature of 80° C. for a period of 120 minutes.

The final catalyst shaped articles had a diameter of 5 mm, a length of 5 mm and a 0.8 mm thick activated outer layer. The breaking strength was 120 N (measured in the radial direction according to ASTM D 4179-82). The catalyst prepared according to the invention was characterized by a considerably reduced bulk density of only 1.2 kg/l as compared with the prior art, but still had sufficient strength for use in catalytic applications.

COMPARISON EXAMPLE 1

A comparison catalyst in accordance with EP 0 648 534 A1 was prepared. Here, the alloy powder from example 1, a cobalt powder with an average particle size of 20 μm and a wax powder (ethylene bisstearoylamide) with an average particle size of 15 μm, as lubricant and pore producer, were used.

The alloy powder and 15 wt. % of cobalt powder, with respect to the alloy powder, were carefully homogenized in a mixer with the addition of water and, after intermediate drying, mixed with 2.5 wt. % of wax powder, with respect to the alloy powder. The material obtained in this way was compressed into tablets with a diameter of 5 mm and a thickness of 5 mm. The tablets were then calcined and activated as described in example 1. The final catalyst has a 0.3 mm thick active outer layer and a bulk density of 2.2 kg/l.

APPLICATION EXAMPLE

The catalyst prepared according to example 1 (C1), the comparison catalyst according to comparison example 1 (CC1) and a commercially available cobalt supported catalyst (cobalt on a siliceous support) (CC2) were tested for catalytic activity during the preparation of 3-aminomethyl-3,5,5-trimethylcyclohexanone (isophorone diamine IPDA) from 3-cyano-3,5,5-trimethylcyclohexanone (isophorone nitrile IPN) in a two-stage process. The process is described in detail in DE 195 40 191 C1. The properties of the catalysts used are listed in table 1.

In the first stage, isophorone nitrile was at least partly converted into 3-cyano-3,5,5-trimethylcyclohexylimine in the presence of an imination catalyst using ammonia and adding methanol, and in the second stage this was hydrogenated and amminated using hydrogen on a cobalt fixed-bed catalyst from table 1 at a temperature of 100° C. and a pressure of 6 Mpa.

Each stage of the preparation of IPDA was performed in a separate reactor, differently from the procedure described in DE 195 40 191 C1. The two reactors, however, were connected in series. They were maintained at a constant temperature by separate oil heating systems.

The first reactor tube had an internal diameter of 20 mm and a length of 250 mm and was filled with 30 ml of a sulphonate group-containing organo-polysiloxane (particle size 0.4 to 1.4 mm; bulk density 525 g/l) as an imination catalyst (see DE patent application 196 27 265.3).

The hydrogenation reactor had an internal diameter of 17 mm and a length of 350 mm and was filled with 150 ml of the particular catalyst being tested during each trial.

The temperature in the first reactor was adjusted to 35° C. and the temperature in the second reactor to 100° C. The pressure in both reactors was 6 Mpa.

The feed solution of IPN (15 wt. %), ammonia (30 wt. %) and methanol (55 wt. %) was pumped from below through the first reaction tube with a mass flow of 80 ml/h; the iminated reaction mixture obtained in that way passed from there to the second reactor. Hydrogen was passed from above into the second reaction tube with a volume flow of 36 l/h, the reactor thus operated as a trickle bed reactor. The product liquid was collected in a settling vessel below the second reactor.

The product mixture obtained was tested for IPDA and corresponding by-products using gas chromatography. The test results are given in table 2.

TABLE 1

Properties of the catalysts

|  | C1 | CC1 | CC2 |
|---|---|---|---|
| Dimensions | 5 Ø × 5 | 5 Ø × 5 | 4.5 Ø × 5 |
| Cobalt [wt. %] | 72 | 81 | 45 |
| Aluminum [wt. %] | 28 | 19 | n.d. |
| Bulk density [Kg/l] | 1.2 | 2.2 | 0.74 |
| Pore volume [cm³/g] | 0.3 | 0.05 | 0.3 |
| Thickness of outer layer [mm] | 0.8 | 0.3 | n.d. |
| Breaking strength [N] | 120 | 300 | 80 | n.d.: not determined

TABLE 2

Results of IPDA preparation

|  | C1 | CC1 | CC2 |
|---|---|---|---|
| IPDA yield | 89.7 | 89.1 | 84.3 |
| Product purity (% IPDA) | 99.9 | 99.75 | 99.85 |

It can be concluded from the results given in table 2 that a slightly higher target product yield is achieved using the catalyst according to the invention with the same catalyst volume. Since, at the same time, less of the unwanted by-products are formed, a greatly improved purity is obtained after purification distillation. Due to its lower bulk density, the costs of the raw materials for the catalyst are greatly reduced compared with the catalyst CC1 prepared according to EP 0 648 534 A1.

Further variations and modifications of the foregoing will be apparent to those skilled in the art and are intended to be encompassed by the claims appended hereto.

German priority document 197 21 897.0 is relied on and incorporated herein by reference.

We claim:

1. A process for preparing an activated metal fixed-bed catalyst, comprising:

mixing at least one alloy powder of a catalyst metal and an extractable alloying component which is free of a pure catalyst metal with a high molecular weight polymer to form a shapable mixture, shaping the mixture to produce a freshly prepared shaped article, thermally treating said article at temperatures between 100 and 300° C. to remove the polymer through decomposition, calcining the freshly prepared shaped article at a temperature of less than 850° C., and activating the shaped article by extracting at least a portion of the extractable alloying component with an alkaline solution, wherein the high molecular weight polymer is a polyoxymethylene homopolymer or copolymer with a melt volume index MVI (according to DIN ISO 1133, measured at 190° C. with a load of 2.16 kg) from 1 to 50.

2. The process according to claim 1, wherein the MVI is in the range from 5 to 13.

3. The process according to claim 1, wherein the MVI is in the range from 6 to 9.

4. The process according to claim 1, wherein the catalyst has an average particle size of 30 to 120 µm, and is added to the polyoxymethylene in an amount of 5 to 100 wt. % with respect to the amount of catalyst in the mixture.

5. The process according to claim 4, wherein the high molecular weight polymer decomposition is in the presence of an acid medium at temperatures between 100 and 300° C., and wherein an approximately constant rate of decomposition of 6 to 10 grams of formaldehyde per kilogram of polyoxymethylene used per minute is set by controlling a rate of heating and/or a rate of addition of the acid medium.

6. The process according to claim 4, wherein the mixing comprises kneading the catalyst alloy and polymer in the form of powders at 180° C. to 250° C. to produce the shapeable mixture.

7. The processing according to claim 6, wherein the catalyst alloy and polymer are kneaded so as to maintain the primary particle size distribution of the alloy substantially unchanged.

8. The process according to claim 6, wherein the shaping is by extrusion, tabletting or compacting.

9. The process according to claim 4, wherein said polymer and said metal alloy are fed separately to an extruder and are mixed together in said extruder.

10. processing according to claim 4, wherein the decomposition of the polymer is accomplished by controlled heating to decompose the polyoxymethylene to substantially formaldehyde, and to drive the formaldehyde out of the article without cracking said article, by vigorous release of gaseous decomposition products.

11. The process according to claim 8, wherein the polymer decomposition of the shaped article is accomplished by the shaped article being first heated to about 100° C., and then heated to about 300° C. in a controlled manner to avoid destroying the article over a time period of 170 to 200 minutes, and thereafter heating to about 800° C.

12. The process according to claim 4, wherein the activating the shaped article by extracting the extractable alloying component comprises treating the articles with a 20 wt. % solution of alkali at a temperature of 80° C. for 120 minutes.

13. A shaped metal fixed-bed catalyst produced by the process according to claim 1.

14. A shaped metal fixed-bed catalyst produced by the process according to claim 5.

15. A shaped metal fixed-bed catalyst, produced by a process comprising:
mixing with a high molecular weight polymer at least one alloy powder, which alloy comprises:
a catalyst metal, and
an extractable alloying component, wherein the alloy is free of unalloyed pure catalyst metal,
shaping the mixture to produce a freshly prepared shaped article,
thermally treating the shaped article at temperatures between 100 and 300° C. to remove the polymer through decomposition,
calcining the freshly prepared shaped article at a temperature of less than 850° C., and
activating the shaped article by extracting at least a portion of the extractable alloying component with an alkaline solution.

16. The shaped metal fixed-bed catalyst according to claim 15, wherein the high molecular weight polymer is a polyoxymethylene homopolymer or copolymer with a melt volume index MVI, according to DIN ISO 1133, measured at 190° C. with a load of 2.16 kg, from 1 to 50.

17. The shaped metal fixed-bed catalyst according to claim 16, wherein the MVI is in the range from 5 to 13.

18. The shaped metal fixed-bed catalyst according to claim 16, wherein the MVI is in the range from 6 to 9.

19. The shaped metal fixed-bed catalyst according to claim 16, wherein the catalyst has an average particle size of 30 to 120 µm, and is mixed with the polyoxymethylene in an amount of 5 to 100 wt. % with respect to the amount of catalyst in the mixture.

20. The shaped metal fixed-bed catalyst according to claim 16, wherein the high molecular weight polymer decomposition is in the presence of an acid medium at temperatures between 100 and 300° C., and wherein an approximately constant rate of decomposition of 6 to 10 grams of formaldehyde per kilogram of polyoxymethylene used per minute is set by controlling a rate of heating and/or a rate of addition of the acid medium.

21. The shaped metal fixed-bed catalyst according to claim 15, wherein the mixing, comprises kneading the catalyst alloy and polymer in the form of powders at 180° C. to 250° C. to produce the shapeable mixture.

22. The shaped metal fixed-bed catalyst according to claim 15, wherein the catalyst alloy and polymer are kneaded so as to maintain the primary particle size distribution of the alloy substantially unchanged.

23. The shaped metal fixed-bed catalyst according to claim 16, wherein the decomposition of the polymer is accomplished by controlled heating to decompose the polyoxymethylene to substantially formaldehyde, and to drive the formaldehyde out of the article without cracking said article, by vigorous release of gaseous decomposition products.

24. The shaped metal fixed-bed catalyst according to claim 15, wherein the polymer decomposition of the shaped article is accomplished by the shaped article being first heated to about 100° C., and then heated to about 300° C. in a controlled manner to avoid destroying the article over a time period of 170 to 200 minutes, and thereafter heating to about 800° C.

25. The shaped metal fixed-bed catalyst according to claim 15, wherein the activating the shaped article by extracting at least a portion of the extractable alloying component comprises treating the articles with a 20 wt. % solution of alkali at a temperature of 80° C. for 120 minutes.

26. A process for preparing an activated metal fixed-bed catalyst, consisting essentially of:
mixing at least one alloy powder of a catalyst metal and an extractable alloying component which is free of a pure catalyst metal with a high molecular weight polymer to form a shapable mixture,
shaping the mixture to produce a freshly prepared shaped article,
thermally treating said article at temperatures between 100 and 300° C. to remove the polymer through decomposition,
calcining the freshly prepared shaped article at a temperature of less than 850° C., and
activating the shaped article by extracting at least a portion of the extractable alloying component with an alkaline solution,
wherein the high molecular weight polymer is a polyoxymethylene homopolymer or copolymer with a melt volume index MVI (according to DIN ISO 1133, measured at 190° C. with a load of 2.16 kg) from 1 to 50.

27. A shaped metal fixed-bed catalyst, produced by a process consisting essentially of:

mixing with a high molecular weight polymer at least one alloy powder, which alloy comprises:
a catalyst metal, and
an extractable alloying component, wherein the alloy is free of unalloyed pure catalyst metal, shaping the mixture to produce a freshly prepared shaped article, thermally treating the shaped article at temperatures between 100 and 300° C. to remove the polymer through decomposition, calcining the freshly prepared shaped article at a temperature of less than 850° C., and activating the shaped article by extracting at least a portion of the extractable alloying component with an alkaline solution.

28. A process for preparing an activated metal fixed-bed catalyst, comprising:

mixing at least one alloy powder of a catalyst metal and an extractable alloying component which is free of a pure catalyst metal with a high molecular weight polymer to form a shapable mixture, shaping the mixture to produce a freshly prepared shaped article, thermally treating said article at temperatures between 100 and 300° C. to remove the polymer through decomposition, calcining the freshly prepared shaped article at a temperature of less than 850° C., and activating the shaped article by extracting at least a portion of the extractable alloying component with an alkaline solution, wherein the high molecular weight polymer is a polyoxymethylene homopolymer or copolymer with a melt volume index MVI (according to DIN ISO 1133, measured at 190° C. with a load of 2.16 kg) from 1 to 50, and wherein the temperature during calcination of the shaped article is restricted to values below 850° C. to ensure that any aluminum oxide formed is present only in the form of $\gamma$-aluminum oxide which is dissolved out of the shaped article during the subsequent activating step.

29. A shaped metal fixed-bed catalyst, produced by a process comprising:

mixing with a high molecular weight polymer at least one alloy powder, which alloy comprises:
a catalyst metal, and
an extractable alloying component, wherein the alloy is free of unalloyed
pure catalyst metal, shaping the mixture to produce a freshly prepared shaped article, thermally treating the shaped article at temperatures between 100 and 300° C. to remove the polymer through decomposition, calcining the freshly prepared shaped article at a temperature of less than 850° C., and activating the shaped article by extracting at least a portion of the extractable alloying component with an alkaline solution, wherein the temperature during calcination of the shaped article is restricted to values below 850° C. to ensure that any aluminum oxide formed is present only in the form of $\gamma$-aluminum oxide which is dissolved out of the shaped article during the subsequent activating step.

* * * * *